US00PP15613P2

(12) United States Plant Patent
Newcombe

(10) Patent No.: US PP15,613 P2
(45) Date of Patent: Mar. 1, 2005

(54) POPLAR TREE NAMED 'GNARLY POPLAR'

(50) Latin Name: *Populus trichocarpa*
Varietal Denomination: Gnarly Poplar

(75) Inventor: Alan George Newcombe, Moscow, ID (US)

(73) Assignee: Idaho Research Foundation, Inc., Moscow, ID (US)

( * ) Notice: Subject to any disclaimer, the term of this patent is extended or adjusted under 35 U.S.C. 154(b) by 0 days.

(21) Appl. No.: 10/749,678

(22) Filed: Dec. 30, 2003

(51) Int. Cl.[7] ..... A01H 5/00
(52) U.S. Cl. ..... Plt./218
(58) Field of Search ..... Plt./218

*Primary Examiner*—Anne Marie Grunberg
*Assistant Examiner*—Annette H Para
(74) *Attorney, Agent, or Firm*—Klarquist Sparkman, LLP

(57) ABSTRACT

A new and distinctive variety of a poplar tree, named 'Gnarly Poplar,' characterized by an attractive zigzag growth habit.

5 Drawing Sheets

Latin name of the genus and species of the plant claimed: *Populus trichocarpa* Torr. and A. Gray (black cottonwood)× *P. maximowiczii* A. Henry (Japanese poplar).
Variety denomination: 'Gnarly Poplar'.

CROSS-REFERENCED TO RELATED APPLICATIONS

None.

STATEMENT REGARDING FEDERALLY SPONSORED RESEARCH OR DEVELOPMENT

None.

BACKGROUND OF THE INVENTION

The present invention relates to a new and distinct hybrid of poplar tree named 'Gnarly Poplar,' which resulted from advanced-generation breeding of two poplar species, *P. trichocarpa* (unpatented) and *P. maximowiczii* (unpatented). *Populus maximowiczii,* or Japanese poplar, was crossed with *Populus trichocarpa,* the native black cottonwood of the Pacific Northwest, to produce a group of first generation (designated $F_1$) trees. In 1996, male and female interspecific, first-generation hybrids were crossed to produce a second generation (designated $F_2$) of male and female trees. The $F_2$ family was propagated in a field experiment that was planted on Vancouver Island, British Columbia in the spring of 1997. In this, second-generation progeny of some 80 or 90 full siblings, one individual tree alone was contorted. This individual tree is my new variety which I have named 'Gnarly Poplar.' This tree was first discovered by the fall of 2000, and was growing in a cultivated area where this Vancouver Island field experiment was being conducted. 'Gnarly Poplar' is ornamental by virtue of its contorted zigzagging branches and trunk undulations.

The 'Gnarly Poplar' variety differs from its parent trees and other poplar trees known to the inventor, primarily because of its contorted habit of growth. The 'Gnarly Poplar' variety produces leaves that are relatively thick and handsome, and insofar as observed as of this time, is disease-free. The tree is upright and graceful, and it is smaller in overall size than its $F_2$ siblings. Like all poplars of its lineage, this contorted clone is vegetatively reproducible. No contorted poplar trees are known to the inventor.

BRIEF SUMMARY OF THE INVENTION

The first asexual propagation of this new variety was performed in the Spring of 2002 at University of Idaho Forest Research Nursery in Moscow, Id. Third-generation, rooted cuttings were planted in a field on Vancouver Island, British Columbia. These asexually propagated trees have been observed to be becoming as contorted as the original tree and other earlier generations of 'Gnarly Poplar.' This demonstrates that the foregoing and all other characteristics and distinctions come true to form and are established and transmitted through succeeding asexual propagations.

Certain characteristics of this variety, may change with changing environmental conditions (such as photoperiod, temperature, moisture, soil conditions, nutrient availability, or other factors). For example, leaf colors may be brighter green if the trees are grown in soil with greater nitrogen concentrations, and may be more yellow when grown in soil containing lesser amounts of nitrogen. Color descriptions and other terminology are used in accordance with their ordinary dictionary descriptions, unless the context clearly indicates otherwise. Color designations (hue/value/chroma) are made with reference to the Munsell Book of Color, Kollmorgen Instruments Corp., 405 Little Britain Road, New Windsor, N.Y. 12553.

BRIEF DESCRIPTION OF THE PHOTOGRAPHS

The accompanying color photographs show typical specimens of the new tree and leaves of this new poplar tree variety and depict the color as nearly true as is reasonably possible to make the same in a color illustration of this character. It should be noted that colors may vary, for example due to lighting conditions at the time the photographs are taken. Therefore, color characteristics of this new variety should be determined with reference to the observations described herein, rather than from the photographs alone.

DETAILED BOTANICAL DESCRIPTION

Figure 1:
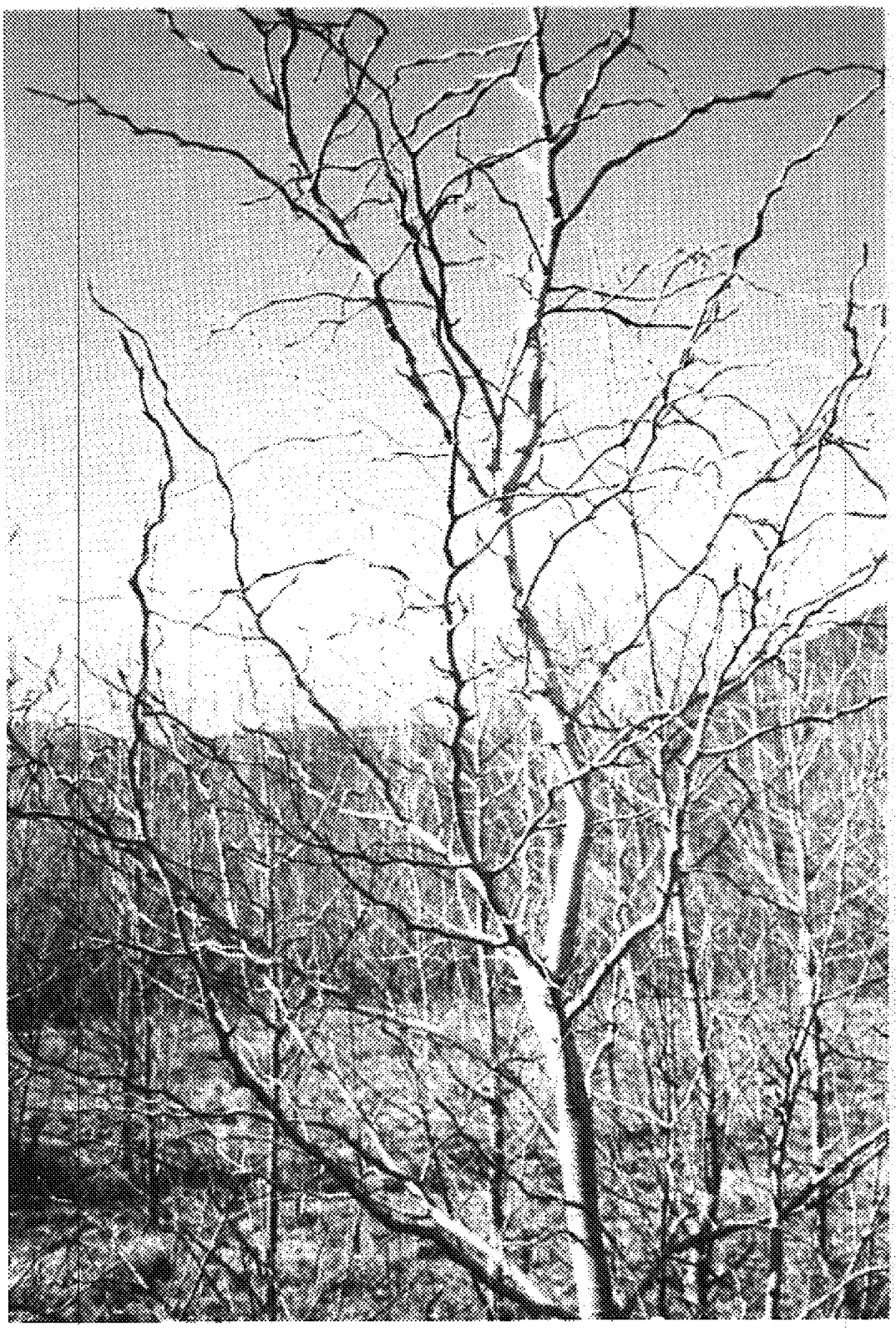
FIG. 1 shows a dormant 'Gnarly Poplar' tree, demonstrating the zigzag type of growth.
Figure 2:
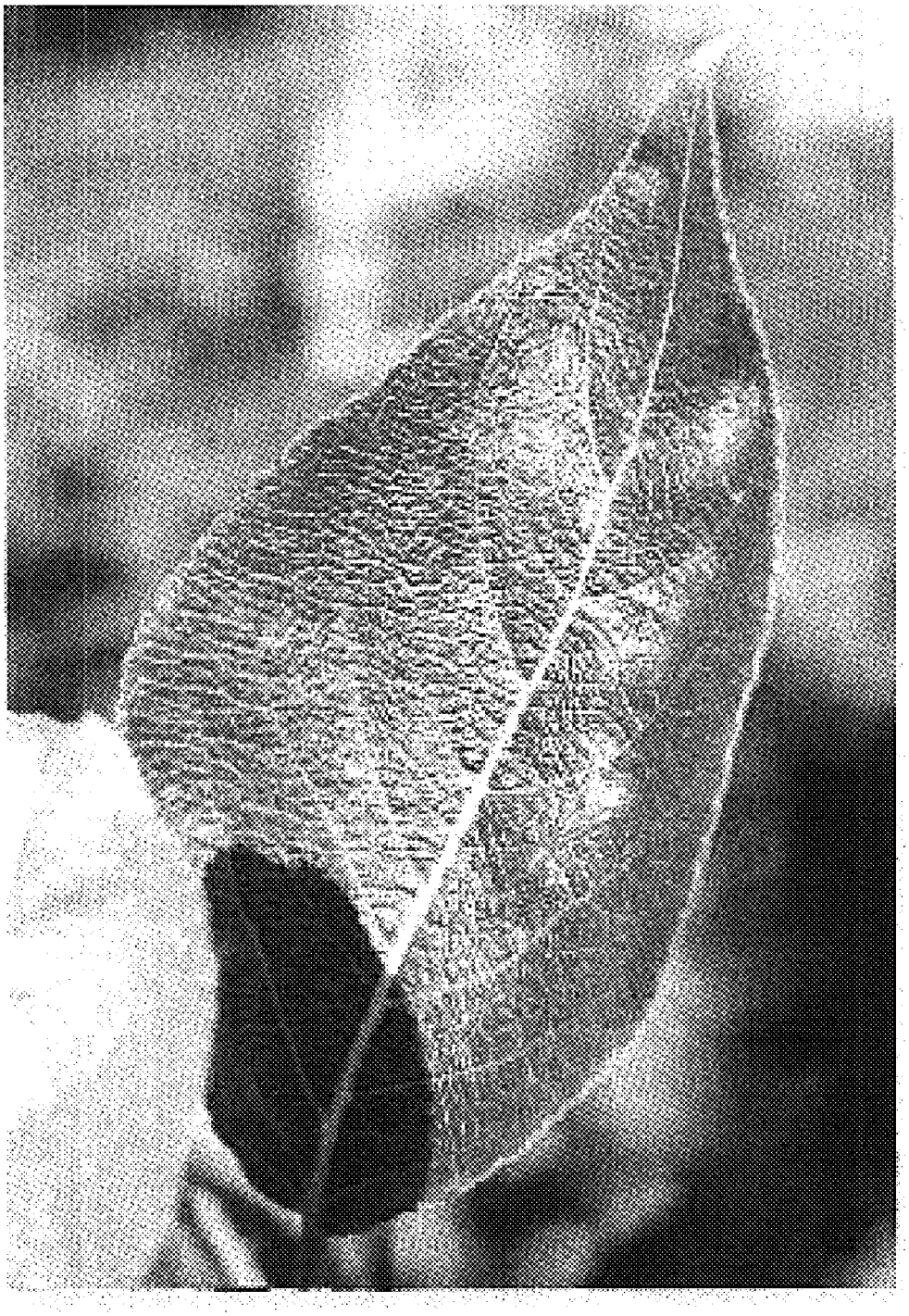
FIG. 2 shows a mature leaf of 'Gnarly Poplar'.
Figure 3:
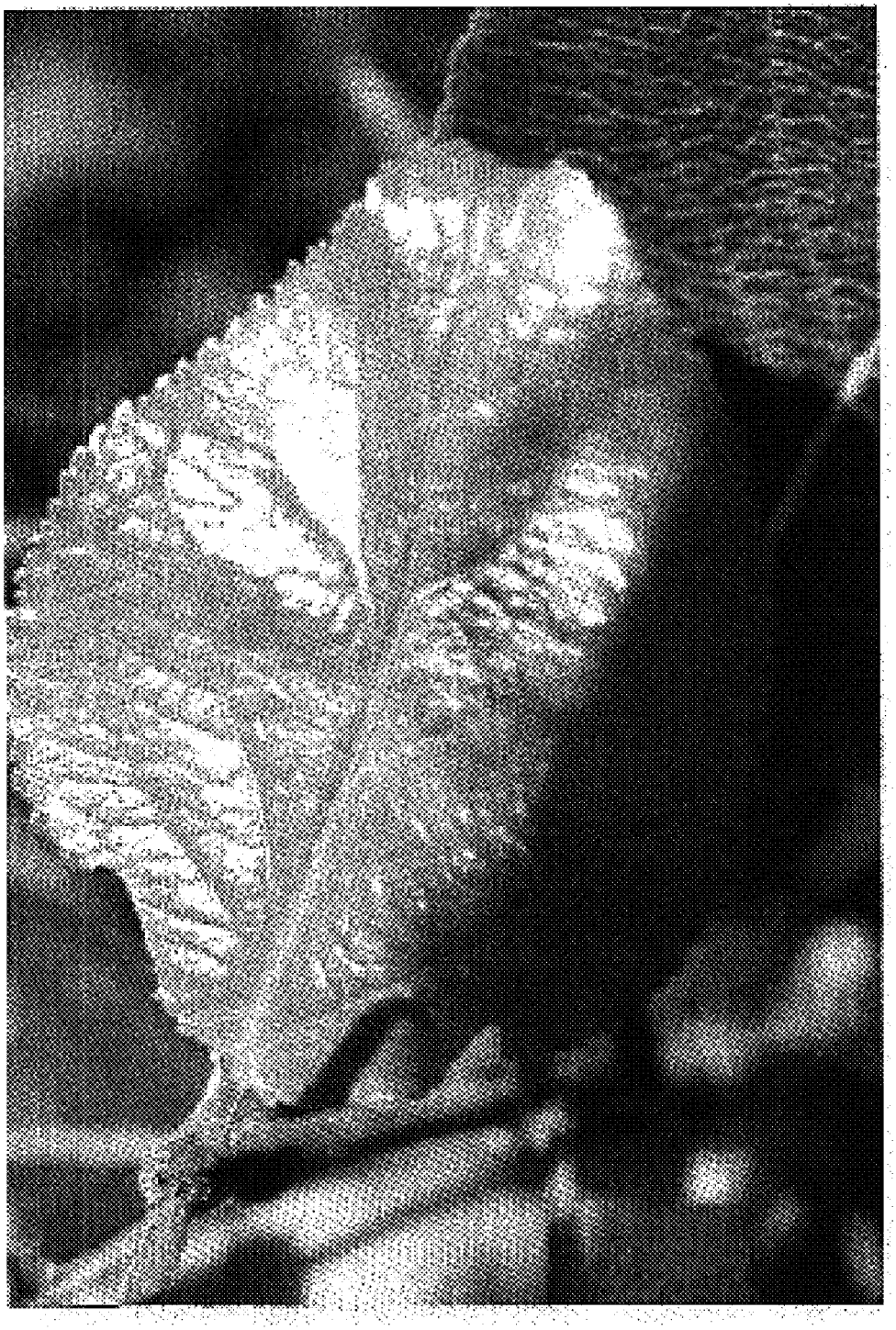
FIG. 3 shows a young leaf of 'Gnarly Poplar'.
Figure 4:
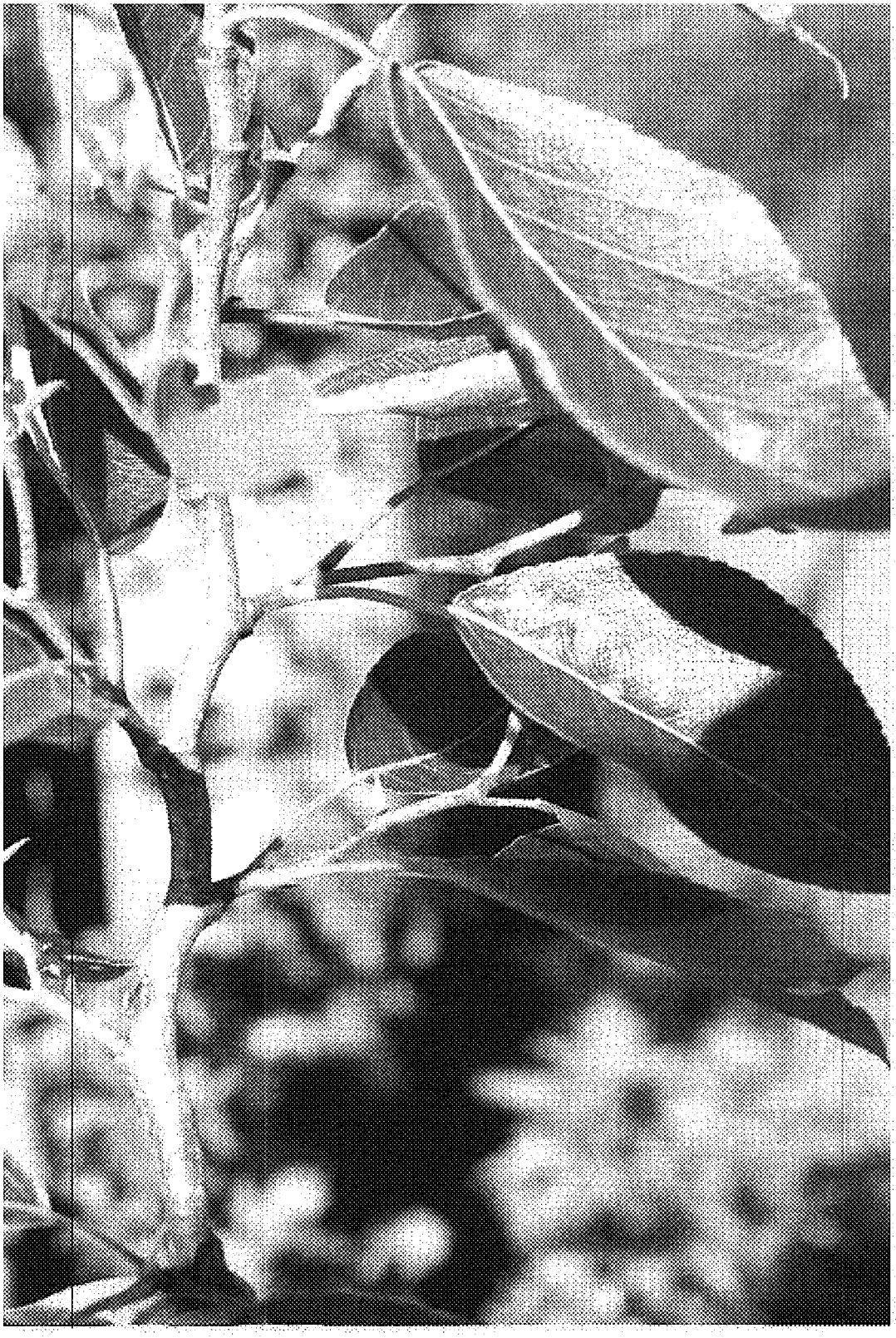
FIG. 4 is shows a section of a one-year shoot, demonstrating the underside of leaf and zigzag branch habit.
Figure 5:
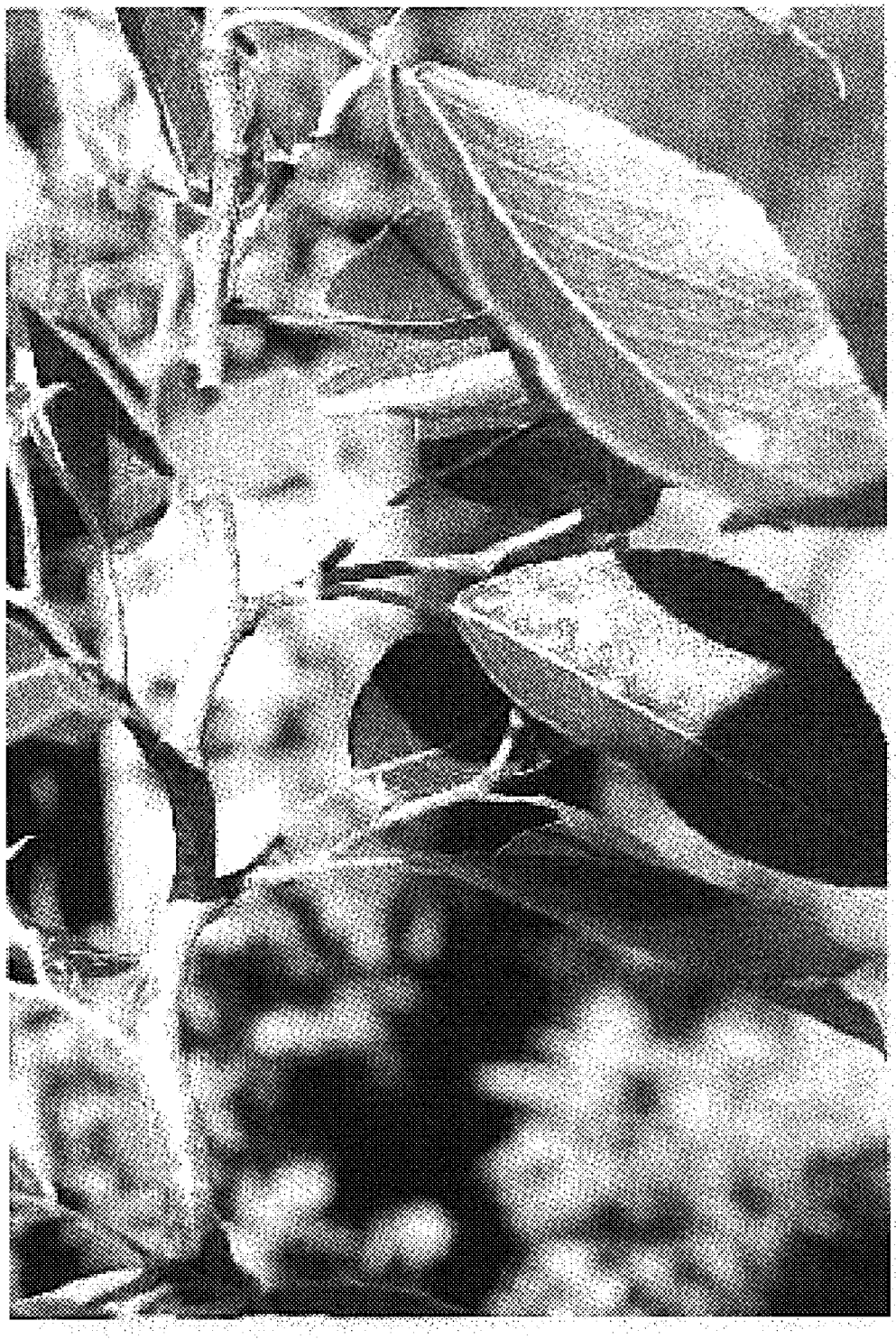
FIG. 5 shows a section of a one-year shoot of 'Gnarly Poplar', demonstrating the upper leaf surface and zigzag habit of growth.

The following detailed description of the 'Gnarly Poplar' cultivar poplar tree is based on observations of the original 'Gnarly Poplar' tree and of subsequent 'Gnarly Poplar' propagants (of various ages, including some which are one year old) on Vancouver Island (British Columbia, Canada), at the University of Idaho in Moscow, Id., and in Wenatchee, Wash.

Scientific name: *Populus trichocarpa*×*P. maximowiczii* 'Gnarly Poplar'.

Parentage: Hybrid clone from interspecific cross.

Botanical Description

Tree:

*Vigor.*—Moderate.

*Height.*—Original tree approximately 4 m in height.

*Width.*—Overall spread of the original tree was about 2 m at about six and one half years of age.

*Overall shape.*—Upright, ellipsoidal; annual growth 0.7 m.

Trunk:

*Size.*—Original tree, caliper about 8.28 cm at 1 m from ground at end of sixth leaf of growth.

*Trunk bark texture.*—Smooth.

*Trunk bark color.*—Light brown (10 R 5/2).

Branches:

*Primary branches.*—Emerge at about 30 degree to 60 degree angles from trunk. Average terminal growth is about 50 cm, zigzag in form. Average diameter of two-year-old branches at base, 15 mm.

*Branch color.*—Two-year-old shoot bark color, medium brown (10 YR 4/6). One-year-old lateral branches, yellow-green (10 Y 7/10).

*Branch pubescence.*—Glabrous.

*Branch lenticels.*—Inconspicuous, one to two per sq cm; light tan (2.5 Y 8.5/2).

*Internodes.*—Average internode length on one-year shoot 3.5 cm (range 2.5 to 5.0 cm).

*Stipules.*—Lacking.

Leaves: (Observations were of ten leaves in August 2003 on trees growing in Moscow, Id.

*Texture.*—Upper surface: very smooth, glossy sheen. Lower surface: smooth, dull, leathery.

*Length.*—Range of 7.5 to 12.0 cm; average 9.8 cm.

*Width.*—Range of 4.0 to 8.5 cm; average 7.5 cm.

*Petiole.*—Twelve to 20 mm in length; average 18 mm; diameter 1 to 2 mm. Color of petiole is reddish purple (7.5 R 2/8) on upper surface, and yellow-green (10 Y 6/6) on lower surface.

*Leaf form.*—Oval, obtuse at base, acute to acuminate at tip. Leaf veins generally alternate but occasionally opposite at base of leaf.

*Leaf color.*—Upper surface medium green (2.5 GY 5/4). Lower surface dull gray-green (2.5 GY 6/2).

*Leaf margin.*—Rounded crenate (5 points per cm).

*Leaf buds.*—Very long (approximately 15 mm), narrow (3 mm at base), pointed; color dull green (2.5 GY 6/6).

Flowers: None observed.

*Sex.*—Poplars are dioecious. Therefore, 'Gnarly Poplar' must be either male or female, but the progeny or ramets of the 'Gnarly Poplar' tree have not yet flowered.

Propagation: Easily propagated by dormant hardwood cuttings and expected to be propagatable by softwood cuttings (mist propagation).

Use: Ornamental, specimen tree, or street tree. Ultimate height is expected to be 10 to 15 m, smaller than either parent.

I claim:

1. A new and distinct variety of poplar tree named 'Gnarly Poplar' substantially as illustrated and described.

* * * * *

UNITED STATES PATENT AND TRADEMARK OFFICE

CERTIFICATE OF CORRECTION

PATENT NO. : PP 15,613 P2
DATED : May 1, 2005
INVENTOR(S) : Alan George Newcombe It is certified that error appears in the above-identified patent and that said Letters Patent is hereby corrected as shown below:

Title page,
Item [50], Latin Name, "*Populus trichocarpa*" should be -- *Populus trichocarpa* Torr. and A. Gray (black cottonwood) x *P. maximowiczii* A. Henry (Japanese poplar) --.

Column 2,
Line 7, "Id" should be -- ID --.

Column 3,
Line 18, "*Populus trichocarpaxP.maximowiczii*" should be -- *Populus trichocarpa* x *P.maximowiczii* --.

Column 4,
Line 8, "Id" should be -- ID --.

Signed and Sealed this

Twelfth Day of July, 2005

JON W. DUDAS
*Director of the United States Patent and Trademark Office*